United States Patent [19]
Rubin et al.

[11] Patent Number: 5,587,309
[45] Date of Patent: Dec. 24, 1996

[54] METHOD OF STIMULATING PROLIFERATION AND DIFFERENTIATION OF HUMAN FETAL PANCREATIC CELLS EX VIVO

[75] Inventors: Jeffrey Rubin, Rockville, Md.; Alberto Hayek, La Jolla, Calif.; Gillian M. Beattie, Poway, Calif.; Timo P. J. Otonkoski, La Jolla, Calif.

[73] Assignees: The United States of America as represented by the Department of Health and Human Services, Washington, D.C.; Whittler Institute for Diabetes and Endocrinology, La Jolla, Calif.

[21] Appl. No.: 235,394

[22] Filed: Apr. 29, 1994

[51] Int. Cl.$^6$ ................ C12N 5/00; C12N 5/02
[52] U.S. Cl. ................ 435/240.2; 435/240.21; 435/240.3; 435/240.31; 435/240.25
[58] Field of Search .............. 435/240.2, 240.21, 435/240.3, 240.31, 240.25

[56] References Cited

U.S. PATENT DOCUMENTS 5,362,716  11/1994  Kmiecik et al. ................ 514/12

OTHER PUBLICATIONS

Rubin et al. "Hepatocyte Growth Factor/Scatter . . . ", *Biophysica Acta*, 1155:357–71; 1993.
Strain "Hepatocyte Growth Factor: Another Ubiquitous Cytokine", *J. Endocrin.*, 137:1–5, 1993.
Andersson et al. "Fetal Pancreatic Transplantation", *Transplantation Review*, 6:1, 20–38, Jan. 1992.
Bhargava et al. "Scatter Factor and Hepatocyte Growth Factor . . . ", *Cell Growth & Different.*, 3:11–20, Jan. 1992.
Defrances et al. "The Presence of Hepatocyte Growth Factor . . . ", *Development*, 116:387–95, 1992.
Furlong "The Biology of Hepatocyte Growth Factor/Scatter Factor", *Bioessays*, 14:9, 613–17, Sep. 1992.
Swenne "Pancreatic Beta–Cell Growth and Diabetes Mellitus", *Diabetologia*, 35: 193–201, 1992.
Tsuda et al. "Immunohistochemical Localization of Hepatocyte . . . ", *Jpn. J. Cancer Res.*, 83:1262–66, Dec. 1992.
Hollerström et al. "Functional Maturation and Proliferation . . . ", *Diabetes*, 40:2, 89–93, Dec. 1991.
Weidner et al. "Evidence for the Identity of Human Scatter Factor . . . ", *Proc. Natl. Acad. Sci.*, 88:7001–05, Aug. 1991.
Gherardi et al. "Hepatocyte Growth Factor–Scatter . . . ", *Commentary, Cancer Cells*, 3:6, 227–32, Jun. 1991.
Wolf et al. "Localization of Hepatocyte Growth Factor In Human and Rat . . . ", *Hepatology*, 14:3, 488–94, May 1991.
Kan et al. "Hepatocyte Growth Factor/Hepatopoietin . . . ", *Biochem. & Biophy. Res. Comm.*, 174:1, 331–37, Jan. 1991.
Furlong et al. "Comparison of Biological and Immunochemical Properties . . . ", *J. Cell Sci.*, 100:173–77, 1991.
Nakamura "Structure and Function of Hepatocyte Growth Factor", *Prog. In Growth Factor Res.*, 3:67–85, 1991.
Gherardi et al. "Hepatocytes and Scatter Factor", *Nature*, 346:228, Jul. 1990.
Tashiro et al. "Deduced Primary Structure of Rat Hepatocyte . . . ", *Proc. Natl. Acad. Sci.*, 87:3200–04, Apr. 1990.
Kinoshita et al. "Marked Increase of HGF mRNA . . . ", *Biochem. & Biophys. Res. Comm.*, 165:3, 1229–34, Dec. 1989.
Nakamura et al. "Molecular Cloning and Expression . . . ", *Letters of Nature*, 342:440–43, Nov. 1989.
Miyazawa, et al. "Molecular Cloning and Sequence Analysis . . . ", *Biochem. & Biophys. Res. Comm.*, 163:2, 967–73, Sep. 1989.
Gohda et al. "Purification and Partial Characterization . . . ", *J. Clin. Invest.*, 81:414–19, Feb. 1988.
Vinik et al, Endocrinology & Metabolism Clinics of North America, vol. 22. No. 4 (Dec. 1993) pp. 875–887.
Moghul et al., Proceedings of the American Assoc. for Cancer Research, 35:125 (Mar. 1994).
Dunger et al., Hormone Metab. Res., 23:201–204 (1991).
Beattie et al., J. Clinical Endocrinology & Metabolism, 73(1):93–98 (1991).
Nielsen, J. H. ACTA Endocrino Logica, Suppl 266:7–39 (1985).
Hulinsky, Transplantation Proceedings, 24 (6):2819 (Dec. 1992).
Adamson et al, The Canadian J. of Chemical Engineering, 64:531–539 (Aug. 1986).
Otonkoski et al, Cell Transplantation, 3(3):218 (Apr. 7, 1994).
Calvo et al., Pancreas 8(6):751 (1993).

*Primary Examiner*—Michael G. Wityshyn
*Assistant Examiner*—Susan M. Dadio
*Attorney, Agent, or Firm*—Foley & Lardner

[57] ABSTRACT

A method of inducing the proliferation and/or differentiation of human fetal pancreatic cells entails contacting such cells in primary culture with Hepatocyte Growth Factor/Scatter Factor, thereby inducing a proliferation of β-epithelial cells, an increase in the number of β-epithelial cells which form islet-like cell clusters, and an increase in insulin production per cell. The method provides increased numbers of functional islet-like cell clusters for transplantation, for example, into Type 1 diabetic patients. The method can be scaled up so as to provide clinically useful numbers of cells for transplantation.

6 Claims, 2 Drawing Sheets

METHOD OF STIMULATING PROLIFERATION AND DIFFERENTIATION OF HUMAN FETAL PANCREATIC CELLS EX VIVO

BACKGROUND OF THE INVENTION

The present invention relates to transplantation of human fetal pancreatic cells to treat Type 1 diabetes mellitus. More particularly, the invention relates to the use of a human cytokine, hepatocyte growth factor/scatter factor, to induce ex vivo the proliferation and differentiation of fetal pancreatic cells prior to their transplantation into a diabetic subject.

Type 1 (insulin-dependent) diabetes mellitus is characterized, inter alia, by a loss of insulin-producing Beta ("β") cells and decompensation of metabolism following autoimmune aggression. Fisenharth, *N. Eng. J. Med.* 314: 1360 (1986); Sweane, *Diabetologia* 35: 193 (1992). Treatments of such patients have included primarily parenteral administration of bovine or porcine insulin or recombinant human insulin. This treatment, however, delays, but does not avoid, the pathological sequelae of this disease, and, in addition, requires multiple daily injections of insulin and/or the use of an indwelling catheter and an insulin pump.

Immunosuppressive treatment of patients, for example, with cyclosporin A or FK506 has also been used, but with only limited success. Immunosuppressive drugs produce toxic side effects, including the potential for infection as the result of suppression of the immune system.

Recently, adult human pancreatic islets have transplanted into patients in order to achieve independence from insulin injections. Scharp et al., *Transplant.* 51:76 (1991); Warnock et al., *Diabetologia* 34: 55 (1991). Despite these advances, the limited number of organ donors, the inadequate islet masses obtainable from most pancreases, and graft rejection problems have conspired to limit the general usefulness of this approach. Ricordi et al., *Transplant.* 53: 407 (1992).

An alternate source of pancreatic islets for transplantation is the fetal pancreas. This tissue is rich in undifferentiated β-cells that can, at least in theory, grow and mature after transplantation. Tuch et al., *Diabetes* 35:464 (1986). While the immature immune system of the fetus reduces the likelihood of fetal islet rejection by the recipient, problems relating to the limited availability of suitable fetal pancreases and to the immaturity of the insulin-producing cells in such tissues continue to hinder success in this approach. For a review, see Andersson, *Transplantation Revs.* 6: 20 (1992).

Hepatocyte Growth Factor ("HGF"), a 87 kDa two-chain glycoprotein cytokine first identified in rodent and human plasma and rodent blood platelets, is a potent hepatocyte mitogen. Rubin et al., *Biochem. Biophys. Acta* 1155: 357 (1993). HGF is apparently identical to a fibroblast secretory protein referred to as Scatter Factor ("SF") known to dissociate and increase the motility of epithelial cells. Gherardi et al., *Nature* 346:228 (1990); Weidner et al., *Proc. Nat'l. Acad. Sci.* (USA) 88:7001 (1991); Furlong et al., *J. Cell Sci.* 100: 173 (1991); Naldini et al., *EMBO J.* 10:2867 (1991); Bhargava et al., *Cell Growth Differ.* 3:11 (1992). For this reason, "HGF/SF" is used here as the abbreviation of the name of this cytokine. For reviews of the biology of HGF/SF, see Strain, *J. Endocrinol.* 137: 1 (1993), Furlong, *BioEssays* 14: 613 (1992), and Rubin et al. (1993), above.

HGF has been purified to homogeneity and sequenced, and its gene has been cloned. Miyazawa et al., *Biochem. Biophys. Res. Commun.* 163: 967 (1989); Rubin et al., *Proc. Nat'l Acad. USA* 88: 415 (1991); Weidner et al., *Sci.* (USA) 88:7001 (1991); Nakamura et al., *FEBS Lett.* 224:311 (1987); Nakamura et al., *Nature* 342:440 (1989) Gohda et al., *J. Clin. Invest.* 81: 414 (1988), all of which are incorporated herein by reference.

Wolf et al., *Hepatology* 14: 488 (1991), identified HGF/SF in adult human pancreatic tissue by immunohistochemistry. However, the identifying signal was strong only in exocrine tissue, very weak in endocrine tissues, with no apparent differences between various cell types. In sharp contrast, Tsuda et al., *Jpn. J. Cancer Res.* 83: 1262 (1992), reported immunohistochemistry studies that identified HGF/SF in adult (human and rat) pancreatic, glucagon-producing A cells, but not in the exocrine pancreas. The authors concluded that this cytokine is primarily produced or stored in the A cells, and it was hypothesized that HGF/SF may act as a growth factor in a paracrine and an endocrine fashion. Yet DeFrances et al., *Development.* 116:387 (1992), demonstrated immunohistochemically the presence of HGF/SF in developing rat fetal pancreas with intense staining in acinar cells.

SUMMARY OF THE INVENTION

It is an object of this invention to provide a method for stimulating the proliferation of human pancreatic β-cells by treating primary cultures of fetal pancreatic tissue with HGF/SF.

It is another object of this invention to provide a method for producing β-epithelial cell-containing islet-like cell clusters from primary cultures of human fetal pancreatic cells by treating such cultures with HGF/SF.

It is yet another object of this invention to provide a method for increasing insulin production in primary cultures of human fetal pancreatic cells by treating such cells with HGF/SF.

It is still another object of this invention to provide a method of preparing quantities of HGF/SF-treated functional human fetal pancreatic β-islet cells in amounts sufficient for transplantation into diabetic patients.

A method for stimulating the ex vivo proliferation and differentiation of human fetal pancreatic β-islet cells, comprising the steps of:

(a) preparing a primary culture of human fetal pancreatic cells; and, (b) contacting said primary culture cells with an effective concentration of HGF/SF with an effective concentration of anti-TGF-β antibodies, for an effective period.

These and other objects aspects will become apparent by reference to the following detailed description of the invention and the appended claims.

DETAILED DESCRIPTION OF THE PREFERRED EMBODIMENTS

Figure 1A:
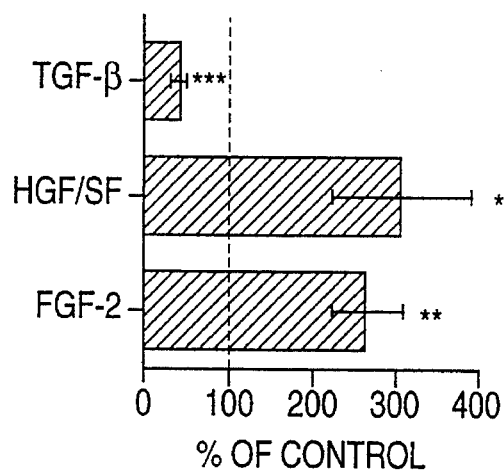
FIGS. 1A–1D are histograms showing the differential effects of HGF/SF, transforming growth factor β and fibroblast growth factor on the yield from human fetal pancreatic cell cultures of islet-like cell clusters (FIG. 1A), of total DNA (FIG. 1B), of total insulin content (FIG. 1C), and of insulin content per unit of DNA content (FIG. 1D).
Figure 1B:
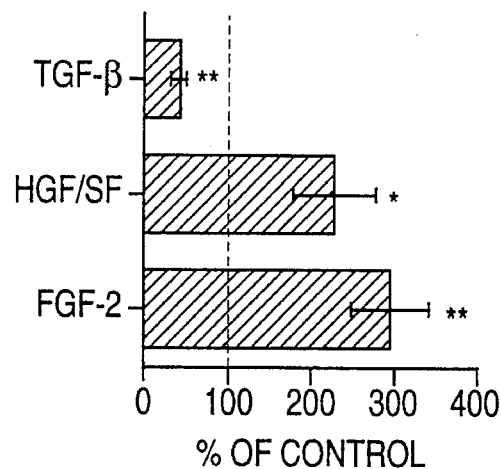
Figure 1C:
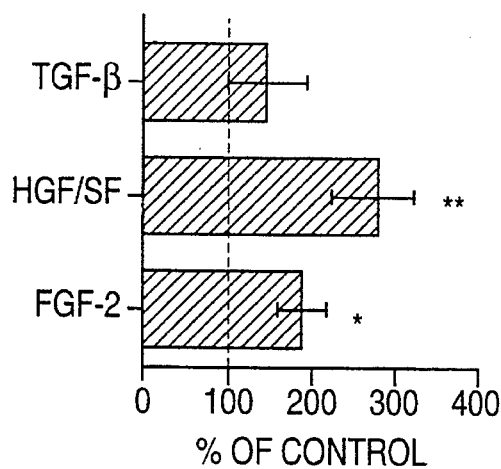
Figure 1D:
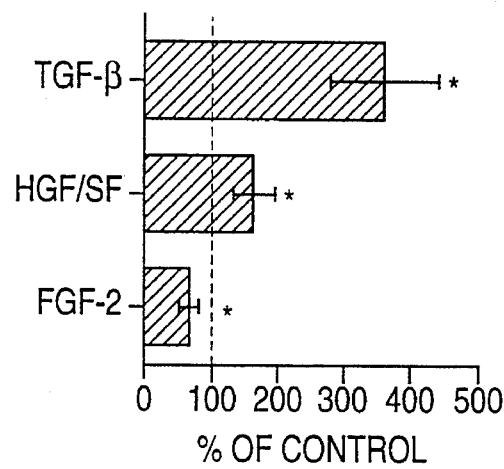

It has been unexpectedly discovered that primary cultures of human fetal pancreatic cells can be induced to proliferate and to differentiate, that is, to produce increased numbers of pancreatiuc cells, to form islet-like cell clusters ("ICC") containing a high percentage of β-epithelial cells, and to increase insulin production per cell, by culturing the primary culture cells ex vivo with an effective concentration of the cytokine HGF/SF for an effective period of time. Such proliferating, differentiated islet-like cell clusters can be used for transplantation into diabetic patients, particularly into diabetics of the Type 1 type.

Expanding such treated fetal pancreatic cultures, increases the supply of functional fetal β-cell islets for transplantation into diabetic patients in clinically useful numbers.

"Primary culture" denotes a mixed cell population of human fetal pancreatic cells that permits interaction of epithelial and mesenchymal cells within ICC. The word "primary" takes its usual meaning in the art of tissue culture.

By "ex vivo" is meant cells that have been taken from a body, temporarily cultured in vitro, and returned to a body.

"Proliferation" indicates an increase in cell number.

"Differentiation" in the present context means increased numbers of islet-like cell clusters containing an increased proportion of β-epithelial cells that produce increased amounts of insulin per cell.

"HGF/SF" is the acronym for hepatocyte growth factor/ scatter factor. An "effective concentration" of HGF/SF is one that will induce primary cultures of human fetal pancreatic cells to proliferate, to form ICC, to increase the number of β-epithelial cells, and to increase insulin production. Preferred concentrations are 5 to 50 ng/ml, most preferred are 15 to 35 ng/ml growth medium. By "effective period" is meant the length of time necessary to observe the aforementioned enhancements.

"FGF-2" refers to basic fibroblast growth factor. "FGF-7" means keratinocyte growth factor. "IGF-II" denotes insulin-like growth factor II. "TGF-β" means transforming growth factor β. "NGF" is the acronym for nerve growth factor. "EGF" means epidermal growth factor. "Ab-1" means monoclonal anti-IGF-1 receptor. "AB-101-NA" means chicken anti-human TGF-β.

Pancreatic Tissue Source

Human fetal pancreases can be obtained at various gestational periods (18 to 24 weeks are preferred) from a non-profit procurement source such as Advanced Bioscience Resource, Oakland, Calif., and The International Institute for the Advancement of Medicine, Exton, Pa. Pancreases should be shipped on ice in a standard culture medium (e.g., RPMI 1640, Irvine Scientific; Irvine, Calif., supplemented with 10% normal human serum and antibiotics (penicillin 100 U/ml, streptomycin 0.1 mg/ml, and amphotericin B 1 mg/ml), and should be received within 18 to 24 h of harvesting.

Tissue Culture

Digestion and culture of pancreases is carried out conventionally as described by Otonkoski et al., *Acta Endocrinol.* 118: 68 (1988), the contents of which are incorporated herein by reference. Briefly, fragments of the tissue are digested with collagenase, for example, collagenase P (product of Boehringer; Indianapolis, Ind.). After being washed in a balanced salt buffer solution, the digested tissue is plated on culture dishes of a type that discourages cell attachment, such as diSPo (product of Baxter, McGraw Park, Ill.), and is cultured in a complete growth medium (e.g., RPMI 1640) supplemented with human serum and antibiotics.

Where multiple variables are to be examined, it is convenient to use sets of dishes, with one dish serving as the control and the remainder serving to test various growth factors.

It is within the scope of this invention to expand cell yield so as to produce clinically useful, that is, bulk quantities, of islet cells for transplantation into patients or other uses by culturing fetal pancreatic cells in a large bioreactor. By "bulk quantities" is meant numbers of cells suitable for transplantation into numbers of patients in order to relieve or ameliorate a disease condition.

In general, in such an expanded culture procedure a commercial-sized bioreactor, such as the OPTICAL™ culture system, Model 5300E (Charles River Labs.; Wilmington, Mass.), or the CELLMAX™ QUAD cell culture system (Cellco, Inc.; Germantown, Md.), is seeded with a primary culture of human fetal pancreatic cells. The bioreactor is perfused with a suitable, complete growth medium supplemented with an appropriately effective concentration of HGF/SF. The β-epithelial cell-containing islet-like clusters are then harvested. Cells may be cryopreserved prior to use. See, for example, Beattie et al., *Transplantation* 56: 1340 (1993), the contents of which are incorporated herein by reference.

Islet Cell Transplantation

The treated pancreatic cells, particularly those that have been induced to form islet-like cell clusters, either freshly harvested or cryopreserved, can be placed in a suitable pharmaceutical vehicle for infusion into patients or experimental models of diabetes. For example, cells are washed with RPMI 1640 medium supplemented with 1 to 10% human serum albumin or with CMRL 1066 medium supplemented with 2 to 3% human serum albumin prior to suspension in a pharmaceutical vehicle. See REMINGTON'S PHARMACEUTICAL SCIENCES, the contents of which is incorporated herein by reference for suitable suspension fluids. Cells then are loaded into syringes, such as 60-ml syringes, for infusion into human patients. See, e.g., Scharp et al. (1991), Warnock et al. (1991), and Ricordi et al. (1992), all above, which are incorporated herein by reference. Suitable routes for infusion of cells into patients include intraportal, intrasplenic, renal subcapsular space and intravenous routes. The kidney route is preferred because it is a relatively immunoprivileged site, and implantation at this site may be less susceptible to endocrinological deterioration. Andersson et al., *Transplantation Revs.* 6: 20 (1992).

In Vitro Incubation Conditions

It is preferred to use 10% human serum with all growth factors except IGF-I, IGF-II or PDGF with which a supplement of 1% human serum, transferrin and bovine serum albumin (BSA) is preferred. The growth medium is changed at suitable intervals, preferably at about 3 days of incubation.

Where it is desired to measure the extent of cell proliferation, at a suitable time after plating, [methyl —$^3$H]-thymidine (Amersham; Arlington, Ill.) can be added to each culture vessel.

Rounded cell aggregates (ICC) can be picked and counted under a stereomicroscope. In order to collect cells for further analysis, these ICC's can be combined with the remaining cells in the dish (isolated by brief low speed centrifugation as described in the examples below). After washing the combined cells with a balanced salt buffer, (such as HBSS), the cells are sonicated, the DNA content measured, (for example, via the fluorometric approach described by Hinegarden, *Anal. Biochem.* 39:192 (1971), and the insulin content measured conventionally, for example by RIA (DPC; Los Angeles, Calif.) on an ethanol extract of the cell sonicate. Incorporation of radioactive thymidine can be determined by liquid scintillation counting.

Bioactive Peptides and Antibodies

Recombinant human IGF-1 and IGF-II (100 ng/ml) may be obtained from The Whittier Institute for Diabetes and Endocrinology, La Jolla, Calif. 92037. Collaborative Research (Bedford, Mass.) is a source of recombinant human PDGF (10 ng/ml), 7s NGF (100 ng/ml), and mouse EGF (25 ng/ml). Recombinant human TGF-α (25 ng/ml) is a product of Sigma (St. Louis, Mo.).

Recombinant human HGF/SF (25 ng/ml) is produced by a baculovirus expression system as follows:

The insect cell line *Spodoptera frugiperda* (Sf9) was obtained from the American Type Culture Collection and grown at 27° C. in EXCELL 400 (JR Scientific) serum free growth medium. *Autographica californica* virus (AcNPV) can be obtained from Dr. M. Summers, Texas A&M University. Sf9 cells were infected with a multiplicity of infection of $\geq 10$ plaque-forming units/cell for protein expression studies and 0.1–10 pfu/cell for virus stock production. The baculotransfer vector pVL941 can be produced according to Luckow et al., *Virology* 170:31 (1989), the contents of which are incorporated herein by reference. To insert human HGF/SF cDNA into pVL941, the full-length coding region of HGF/SF was generated by polymerase chain reaction (PCR) using Bam Hi restriction enzyme-tagged oligonucleotide primers. PCR amplified product was cleaved with Bam H1 and subcloned into the Bam H1 site of the baculovirus vector pVL941. Recombinant baculovirus was produced by cotransfecting Sf9 insect cells with AcNPVDNA (1 mg) and pVL-HGF (2 mg) by calcium phosphate transfection. The resulting culture supernatant fluids were harvested after 4 days, and screened for homologous recombination by visual inspection and dot-blot hybridization using a 32P-labeled, nick-translated HGF cDNA probe. Purified recombinant baculovirus was obtained after 3 rounds of plaque purification. For the expression of recombinant HGF/SF, Sf9 cells were infected with the recombinant baculovirus grown in medium, such as EXCELL 400, for 3 days. The resulting conditioned medium was harvested, clarified by centrifugation at 1000× g for 10 mins., and stored frozen at −20° C. Subsequently, the medium was thawed, and concentrated by ultrafiltration (YM filter, 10 kDa cutoff, Amicon). The recombinant HGF/SF in the concentrate was purified by heparin affinity chromatography essentially as previously described. Rubin et al., *Proc Natl. Acad. Sci.* USA 88:415 (1991).

Recombinant human FGF-2 (50 ng/ml) is made according to Isaachi et al., *Proc. Nat'l Acad. Sci.* (USA) 88:2628 (1991), the contents of which is incorporated herein by reference.

Recombinant human KGF/FGF-7 (50 ng/ml) is produced according to Ron et al., *J. Biol. Chem.* 268:2984 (1993), which is incorporated herein by reference.

Monoclonal anti-IGF-1 receptor (2 μg/ml) is obtained from Oncogene Science (Uniondale, N.Y.), and chicken anti-h TGF-β (5 μg/ml) from R & D Systems (Minneapolis, Minn.).

Immunohistochemistry and Morphometry

ICCs can be incubated with bromodeoxyuridine ("BrdU"), fixed in formaldehyde, embedded in paraffin and sectioned. Sections can be stained for insulin using an immunoalkaline phosphatase technique (see, e.g., Erber et al., *Am. J. Clin. Path.* 88: 43 (1987) which is incorporated herein by reference) using polyclonal guinea pig anti-porcine insulin (Chemicon; El Sequndo, Calif.) as the primary antibody.

Cell nuclei that have incorporated BrdU during DNA synthesis can be identified using mouse monoclonal anti-BrdU (Dako; Carpintaria, Calif.), detected with the immunoperoxide technique (Sternberger et al., *J. Histochem., Cytochem.* 18: 315 (1970)), followed by hematoxylin counterstaining.

Epithelial cells can be identified on separate sections using a mouse monoclonal anti-epithelial antigen antibody (Ber-EP4, Dako, above) as the primary antibody.

Surface areas of insulin-positive and epithelial cells, calculated as percent of the total ICC area, can be quantified with a computerized image analyzer (American Innovision; San Diego, Calif.). The same method can be used for the determination of the BrdU labeling index. Cells positive for both insulin and BrdU may also be recorded in separate sections of the same samples after double staining of the two antigens.

Mean cell size can be calculated by the ratio of total ICC area to the number of nuclei.

Mean β-cell size can be estimated by measuring the surface area of individual insulin-positive cells.

A sufficient number of ICC sections (at least 15) and nuclei (at least 1000) should be analyzed for each sample to correct for biological and experimental variability of the samples.

The present invention is described further by reference to the following illustrative examples that should not in any way be construed as limiting the scope of the invention which is defined by the specification and appended claims.

EXAMPLE 1

Generation of ICCs

Pancreases were dissected free of surrounding tissue and cut into 4 equally sized pieces. Tissues were then blotted, weighed, and cut into small pieces (1 mm³), Fragments were digested for 15 mins. in a shaking water bath (37° C., 200 osci/min) in Hank's balanced salt solution ("HBSS") containing 5.5 mg/ml collagenase P. Digested tissues were washed twice in cold HBSS and plated (¼ pancreas/dish) on 60 mm petri dishes of a type that encourages cell attachment, in RPMI 1640 with 10% HSA and antibiotics. One of the dishes served as the control, and growth factors were added to the others. As noted above, the human serum albumin content of the medium was reduced to 1% in the case of IGF-I, IGF-II or PDGF, and the medium supplemented with 10 μg/ml transferrin and 0.1% BSA. Medium (with the additions) was changed after 3 days.

On the 5th day, 0.5 μCi/ml of labeled thymidine (5.0 Ci/mmol.) was added to each dish. After a 16 hr incubation, all well-formed rounded cell aggregates (ICCs) were picked and counted as described above.

The average number of ICCs harvested from control cultures in 10% HSA was 13.4 per mg of starting tissue (Table 1). The yield of tissue was not affected by the gestational age. Based on an analysis of 383 pancreases, the mean weight of pancreas was 102 mg at 18 wk and 247 mg at 24 wk. This implies that in this age range the average yield of ICCs was 1400–3300 per pancreas. The yield was slightly, but significantly, lower in 1% HSA (9.2 vs. 13.4 ICC/mg, Table 1).

Total DNA syntheses, as measured by $^3$H-thymidine incorporation at the end of the culture period, paralleled the results obtained by ICC numbers and DNA content.

TABLE 1

Effect of growth factors on the yield, DNA content and insulin content of ICCs.

| Culture conditions | N | Number of ICCs (per mg tissue) | DNA content (per mg tissue) | Insulin content (per mg tissue) | Insulin content (per μg DNA) |
|---|---|---|---|---|---|
| 10% HS | 41 | 13.4 (11.3–15.4) (100%) | 409 ng (335–483) (100%) | 0.8 pmol (0.6–1.1) (100%) | 2.9 pmol (1.6–4.2) (100%) |
| FGF-2 50 ng/ml | 11 | 265 (160–371)** | 302 (200–404)** | 187 (120–254)* | 70 (44–97)* |
| FGF-7 50 ng/ml | 9 | 131 (113–150)** | 166 (107–224)* | 95 (68–122) | 54 (34–74)** |
| HGF/SF 25 ng/ml | 9 | 308 (113–503)* | 233 (120–346)* | 280 (178–381)** | 165 (100–230)* |
| TGF-α 25 ng/ml | 6 | 192 (94–289) | 150 (92–209) | 144 (68–220) | 95 (71–120) |
| EGF 25 ng/ml | 6 | 136 (82–190) | 137 (46–228) | 188 (51–383) | 120 (73–167) |
| TGF-β 10 ng/ml | 6 | 43 (26–61)*** | 44 (16–72)** | 147 (25–268) | 360 (150–571)* |
| NGF 100 ng/ml | 8 | 121 (88–155) | 107 (62–204) | 186 (40–353) | 145 (72–217) |
| 1% HS | 12 | 9.2 (6.9–11.2) (100%) | 323 ng (216–407) (100%) | 0.5 pmol (0.3–0.8) (100%) | 2.0 pmol (0.7–3.2) (100%) |
| IGF-I 100 ng/ml\ | 7 | 148 (90–207) | 147 (87–209) | 174 (100–250)* | 127 (86–167) |
| IGF-II 100 ng/ml\ | 7 | 155 (103–206)* | 135 (84–187) | 145 (91–197) | 115 (60–171) |
| PDGF 10 ng/ml\ | 9 | 149 (78–219) | 147 (62–232) | 133 (44–223) | 115 (50–180) |

Pancreases were divided in four parts and cultured for 6 days in either control or experimental media. Tissue weight refers to the original weight before culture and DNA content to the final content after culture. Absolute values are shown for the controls; effects of growth factors are expressed as percent of each individual control (mean and 95% CI).
\cultured in 1% human serum (all other growth factors used in 10% serum).
*, $p < 0.05$; **, $p < 0.01$; $p < 0.001$, as compared with the hypothesized population mean (=100) with the two-tailed one sample t test.

EXAMPLE 2

Effect of Growth Factors on Yield of ICCs

The growth factors having a stimulating effect on the ICC yield included HGF/SF, IGF-II, FGF-2 and FGF-7 at the concentrations shown in Table 1. The effects of TGF-α, EGF, NGF, IGF-I and PDGF were not significant. TGF-β had a potent inhibitory effect, unlike any other factors tested (Table 1).

The most potent stimulatory growth factor was HGF/SF (about 3-fold increase in ICC number). The ICCs formed in the presence of HGF/SF were generally more translucent and rounded than controls.

Although FGF-2 was nearly as potent a stimulator of ICC formation of HGF/SF (about a 2.6-fold increase), this appeared to induce the formation of 2 different types of ICCs: small translucent ones (shown by immunostaining to be mostly epithelial), and larger, more dense clusters containing primarily non-epithelial cells. FGF-7 was least effective.

To collect total cells, ICCs were combined with the small cell pellet from the dish isolated by centrifugation at 800×g for 3 mins. After 2 washes in HBSS, the cells were homogenized by sonication. DNA was analyzed flurometrically (see above).

There were no significant differences in the average DNA content/ICC (mean of controls 34 ng per ICC). The total amount of DNA, as an estimate of total cell number, reflected well the results calculated from the ICC (Table 1).

EXAMPLE 3

Effects of Growth Factors on Insulin Contents

Insulin was measured by a commercial solid phase RIA kit after 16 hr acid ethanol extraction at +4° C. The assay Cv was 8.3 and 12.2% for control samples containing 136 and 28 μU/ml insulin, respectively.

In contrast to the effects on cell-growth, the insulin contents were similar in 1 and 10% HSA (Table 1).

Most of the growth factors tested were without effect on total insulin content of the cells. HGF/SF, FGF-2 and IGF-1 were the only factors that increased the total content of insulin in this respect. HGF/SF clearly is the most potent, causing a 180% increase. A fundamental difference between HGF/SF and FGF-2 was observed; the latter actually decreased the insulin content per DNA (per cell) by 30%, whereas the former induced a 65% increase in the same parameter (Table 1, FIG. 1). FGF-7 caused an even stronger decrease in the insulin content per DNA than did FGF-2.

The total insulin content was not affected by TGF-β, but, as the result of dramatic decrease in total DNA caused by this factor, the insulin content per DNA was increased by 3.6 fold (Table 2, FIG. 1).

EXAMPLE 4

Effects of Antibodies

As expected, the neutralizing TGF-β antibody had an effect opposite that of the antigen itself, suggesting that either the ICCs or serum-containing medium may have been a source of TGF-β. The ICC yield was increased and DNA synthesis stimulated by the TGF-β antibody. There was also a 61% increase in the total insulin content (Table 2).

TABLE 2

Effect of polyclonal TGF-β antibody and monoclonal IGF-I receptor antibody on the development of ICCs, DNA synthesis and insulin content after 5 days of culture.

|  | anti-IGF-I-R (n = 3) | anti-TGF-β (n = 5) |
|---|---|---|
| ICC yield per mg tissue | 64 (32–86)* | 183 (145–221)** |
| DNA content per mg tissue | 82 (6–169) | 196 (62–330) |
| $^3$H-Thymidine incorporation |  |  |
| per mg tissue | 70 (0–161) | 173 (101–251)* |
| per DNA | 84 (25–141) | 96 (66–124) |
| Insulin content |  |  |
| per mg tissue | 89 (0–239) | 161 (99–224)* |
| per DNA | 107 (0–217) | 106 (17–194) |

Data are expressed as percent of control ICCs originating from the same pancreas and cultured without added antibody in medium containing 10% HS (mean and 95% CI).
*, **, $p < 0.05, 0.01$, one group t-test (population mean = 100)

In order to test whether the relatively weak effects of exogenous IGFs were due to the presence of endogenous IGFs, the IGF-1 receptor was blocked with a neutralizing antibody. In contrast to the effect of the TGF-β antibody, there was a significant (36%) decrease in the number of ICCs, whereas DNA synthesis and insulin levels were not affected (Table 2).

EXAMPLE 5

Morphometry

The three most potent growth factors (HGF/SF, FGF-2 and TGF-β) were studied for their effects on the cell populations contained within the ICCs. Based on the epithelial cell content after 7 days in culture, it was apparent that only HGF/SF had stimulated the growth of epithelial cells. In contrast, the proportion of epithelial cells was 50% lower after culture with either FGF-2 or TGF-β (Table 3). Together with the data presented above, this implies that FGF-2 mainly stimulated the growth of non-epithelial cells, and that the growth-inhibitory action of TGF-β was primarily targeted on epithelial cells. In the FGF-2-treated cultures, the non-epithelial cells were mainly found in large (>100 μm) rounded cell clusters consisting of relatively small cells, whereas in the TGF-β-treated cultures the non-epithelial cells were often seen centrally in irregularly shaped cell clusters with epithelial and insulin-positive cells in the periphery.

In the control cultures, insulin staining was usually found in single cells or in small groups of positive cells scattered within the ICCs; occasionally, however, the staining was seen in cell groups appearing to bud out of the ICC. These insulin-positive outgrowths were more commonly encountered in the HGF/SF-treated ICCs. Insulin-positive cells accounted for 4% of the total cell surface area in sections of the control ICCs. FGF-2- and TGF-β-treated ICCs did not differ from the controls, whereas the insulin-positive area of HGF/SF-treated ICCs was 2.3-fold higher (9.4% vs. 4.0%, p<0.01; Table 3). The mean cell size was not different in HGF/SF-treated and control ICCs (62.1 vs. 69.3 μm$^2$, respectively). As only less than 10% of these cells represented β-cells, the sizes of individual insulin-positive cells were also measured. The mean size of insulin-positive cells was 1.6-fold higher than the average cell size. Again, there were no differences between HGF/SF-treated and control cells (110 vs. 108 μm$^2$, respectively).

Figure 2:
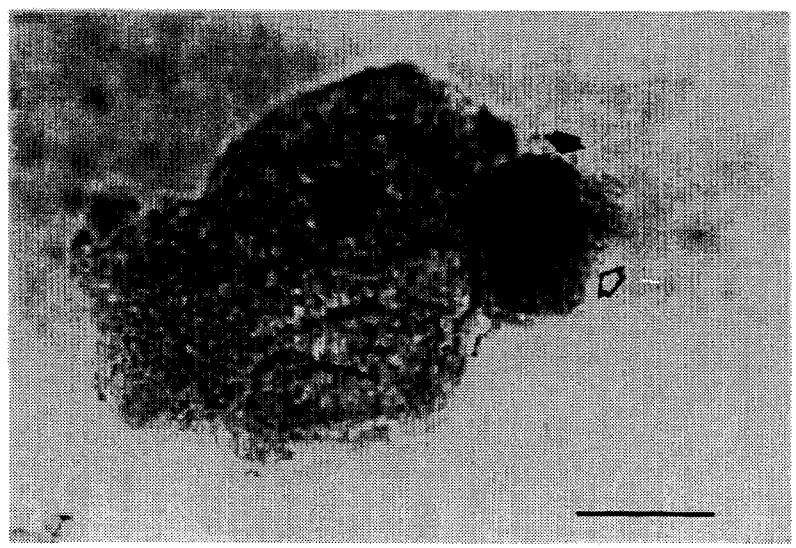
FIG. 2 demonstrates β-islet cell replication in HGF/SF-treated ICCs by double immunostaining for BrdU (black arrows) and insulin (open arrows) which detects cells positive for both antigens.

BrdU labeling of FGF-2-treated ICCs was almost twice as high as that of controls (6.9 vs. 3.7%, p<0.05, Table 3). The labeling of HGF/SF-treated ICCs was nearly as high as after FGF-2 treatment (6.3%). The Labeling Index of TGF-β-treated ICCs was significantly lower (1.9%, p<0.05) confirming the results obtained with $^3$H-thymidine incorporation. Cells positive for both insulin and BrdU were scarce, accounting for only 2.5% of all BrdU-labelled cells in control cultures. HGF/SF markedly increased the BrdU labeling of insulin-positive cells (7.4% of all labelled cells, p<0.01, Table 3, FIG. 2).

TABLE 3

Morphometric analysis of cell populations in the ICCs after 6 days of culture with growth factors.

|  | Control | HGF/SF | FGF-2 | TGF-β |
|---|---|---|---|---|
| Epithelial cells | 55.7 ± | 64.5 ± | 28.3 ± | 38.6 ± |
| (% of surface area) | 2.0 | 2.8 | 2.1* | 8.1* |
| Insulin cells | 4.04 ± | 9.38 ± | 3.39 ± | 6.05 ± |
| (% of surface area) | 0.73 | 1.14* | 0.78 | 1.04 |
| BrdU labelling index | 3.68 ± | 6.34 ± | 6.85 ± | 1.88 ± |
| (%) | 0.53 | 1.31 | 0.96* | 0.29 |
| Insulin + BrdU double positive cells of total BrdU cells | 10 of 408 (2.45%) | 27 of 363# (7.44%) | 11 of 597 (1.84%) | 1 of 114 (0.88%) |

Values are the means ± S.E.M. of 4 separate experiments, except for insulin/BrdU double positive cells, which are expressed as total numbers of nuclei detected in the 4 sections.
Significant differences between groups are indicated as follows:
*, $p < 0.05$, as compared with control (Fisher's PLSD test after one-way analysis of variance)
, $p < 0.01$, as compared with control (Chi-square test)

EXAMPLE 6

Use of HGF/SF to Increase Transplantable Human Fetal Islet Tissues

HGF/SF- or FGF-2-induced ICCs (500), produced as in the preceding examples, and 500 control ICCs were transplanted under the kidney capsule of nude mice. The treated clusters developed into functional islet tissue, as judged by human C-peptide response to a glucose challenge (control 6.2-fold; HGF/SF 5.0-fold; FGF-2 1.9-fold). However, the absolute level and response of the serum C-peptide was significantly (p<0.01) lower with FGF-2-treated grafts, whereas HGF/SF-treated grafts were functionally and morphologically identical with normal controls.

Thus, HGF/SF pretreatment of human fetal pancreatic cells intended for transplantation results in significant increases in the transplantable cell mass.

Accordingly, among the peptide growth factors screened for their mitogenic, morphogenic and insulinotropic action in cultures consisting of mixed human fetal pancreatic cells, it was found that HGF/SF is the most potent stimulus for ICC formation from fetal pancreatic cells, and, most importantly, that HGF/SF is the only factor that increases the epithelial, β-cell and insulin content of the cells. The BrdU experiments confirmed the mitogenic effect of HGF/SF on β-cells or their precursors. By contrast, TGF-β has an endogenous anti-proliferative effect on pancreatic epithelial cells.

These data establish that HGF/SF is useful in generating a more-abundant and more-differentiated source of islet cells or their precursors for use in treating a patient with Type 1 diabetes mellitus by islet cell transplantation. In a typical procedure, primary cultures of human fetal pancreatic cells are contacted with HGF/SF, without or with anti-TGF-β human or humanized antibodies, under conditions such that the β-cells in such cultures proliferate and differentiate into insulin-producing islet cell clusters containing a large proportion (e.g., 50%) of β-epithelial cells, and the cultures then administered to the patient parenterally, for example, by an intraportal, intrasplenic, renal subcapsular or intravenous route.

What is claimed is:

1. A method for inducing the ex vivo proliferation and differentiation of human fetal pancreatic β-islet cells, comprising the steps of:

(a) preparing a primary culture of human fetal pancreatic cells; and (b) contacting said primary culture with an effective concentration of Hepatocyte Growth Factor/Scatter Factor, wherein said effective concentration is an amount sufficient to induce said primary culture to proliferate, to form insulin-producing islet-like cell clusters that upon grafting into a host animal develop into functional islet tissue, and to increase the proportion of β-epithelial cells in said clusters.

2. The method of claim 1, wherein said cell proliferation and differentiation comprise an increase in insulin production per cell.

3. A method of claim 1, wherein said effective concentration of Hepatocyte Growth Factor/Scatter Factor ranges from about 5 to about 50 ng/ml.

4. The method of claim 1, further comprising contacting said primary culture with an amount of anti-Tumor Growth Factor β antibody sufficient to increase cell proliferation and formation of islet-like pancreatic cell clusters.

5. The method of producing proliferating and differentiating human fetal pancreatic islet cells in clinically useful quantities, comprising the steps of:

(a) preparing a primary culture of human fetal pancreatic cells;

(b) seeding said primary culture into a bioreactor;

(c) perfusing said bioreactor with a complete growth medium supplemented with an effective concentration of Hepatocyte Growth Factor/Scatter Factor, wherein said effective concentration is an amount sufficient to induce said primary culture of human fetal pancreatic cells to proliferate, to form insulin-producing islet-like cell clusters that upon grafting into a host animal produces functional islet tissue, and to increase the proportion of β-epithelial cells in said clusters; and (d) harvesting said islet-like cell clusters.

6. The method of claim 5, further comprising contacting said primary culture with an amount of anti-Tumor Growth Factor β antibody sufficient to increase cell proliferation and formation of islet-like pancreatic cell clusters.

* * * * *